United States Patent
Shoji et al.

(10) Patent No.: US 6,835,709 B2
(45) Date of Patent: Dec. 28, 2004

(54) STIMULATIVE AGENT AND STIMULATIVE PERFUME COMPOSITION

(75) Inventors: Ken Shoji, Yokohama (JP); Seiichi Hirose, Yokohama (JP); Sumie Taguchi, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 10/197,908

(22) Filed: Jul. 19, 2002

(65) Prior Publication Data

US 2003/0069166 A1 Apr. 10, 2003

Related U.S. Application Data

(63) Continuation of application No. 09/613,332, filed on Jul. 7, 2000, now abandoned.

(30) Foreign Application Priority Data

Jul. 9, 1999 (JP) .............................................. 11-196295

(51) Int. Cl.[7] .............................................. A61K 7/46
(52) U.S. Cl. ............................................ 512/27; 512/1
(58) Field of Search ....................................... 512/1, 27

(56) References Cited

U.S. PATENT DOCUMENTS

| | | | |
|---|---|---|---|
| 4,020,156 A | * | 4/1977 | Murray et al. ............. 424/76.6 |
| 4,045,551 A | | 8/1977 | Ueno et al. |
| 4,292,210 A | | 9/1981 | Blume et al. |
| 4,420,472 A | | 12/1983 | Boden et al. |
| 4,492,645 A | * | 1/1985 | Sprecker et al. ............... 512/4 |
| 4,649,044 A | | 3/1987 | Gomi et al. |
| 4,670,463 A | | 6/1987 | Warren et al. |
| 4,995,407 A | | 2/1991 | Kossiakoff et al. |
| 5,141,666 A | * | 8/1992 | Yorozu et al. .............. 510/102 |
| 6,322,838 B1 | | 11/2001 | Guntert et al. |

FOREIGN PATENT DOCUMENTS

| | | | |
|---|---|---|---|
| DE | 3931150 A | * | 3/1991 |
| JP | 01254629 | | 10/1989 |
| JP | 01254629 A | | 10/1989 |
| JP | 06024952 | | 2/1994 |
| JP | 06172781 | | 6/1994 |

OTHER PUBLICATIONS

Arctander, S., "Perfume and Flavor Chemicals (Aroma Chemicals) A–J," 1969, pp. 241–242, S. Arctander, Montclair, N.J., USA, XP002235168.

Buchbauer, G. et al., "Fragrance Compounds and Essential Oils with Sedative Effects Upon Inhalation," *Journal of Pharmaceutical Sciences*, Jun. 1993, pp. 660–664, vol. 82, No. 6, American Pharmaceutical Association, Washington, D.C., XP000960638.

* cited by examiner

*Primary Examiner*—Jill Warden
*Assistant Examiner*—Monique T. Cole
(74) *Attorney, Agent, or Firm*—Snider & Associates; Ronald R. Snider

(57) ABSTRACT

A stimulative perfume composition which demonstrates an excellent stimulative effect uses an anisaldehyde as the stimulative agent. The stimulative perfume composition includes an effective amount of the anisaldehyde in perfume ingredients.

9 Claims, 2 Drawing Sheets

STIMULATIVE AGENT AND STIMULATIVE PERFUME COMPOSITION

RELATED APPLICATIONS

This application claims the priority of Japanese Patent Application No. 11-196295 filed on Jul. 9, 1999 which is incorporated herein by reference. This application is a Continuation of application Ser. No. 09/613,332, filed on Jul. 7, 2000 and abandoned on Jul. 22, 2002.

FIELD OF THE INVENTION

The present invention relates to a stimulative agent and a stimulative perfume composition and, in particular, to the stimulative agent and the stimulative perfume composition which gives a mental stimulative effect by inhaling the evaporated effective ingredient.

BACKGROUND OF THE INVENTION

The stress in modem society is expressed with various kinds physiological, psychological modes such as the psychosomatic disease of depression. However, the expression for these modes does not necessarily reach a morbid condition. Accordingly, for such modes there is a limit to antidepressant drugs that the supervising physician can use. Also, the general use for drugs such as oral administration or injection administration becomes a new stress. The antidepressant drugs cannot be used for healthy persons. Those who want a stimulative effect in daily life generally use substances such as coffee and cigarettes. However, if these are habitually used, bodily damage may occur.

Thereupon, in conventional aroma therapy, the stimulative effect is obtained by using a certain kind of natural essential oil that has an awakening effect. This has an advantage that it does not add new stress to the human body.

However, selection of the essential oil the stimulative effect is by the empirical judgment of an expert. Since essential oils that show both a stimulative effect and a sedative effect also exist, the effect in essential oils is not clear. Further big individual differences for manifestation of the effect have been observed. The differences are caused by the natural essential oil in aroma therapy which consists of various complicated ingredients. These natural essential oils were not complete as a stimulative agent and a stimulative perfume composition. Thereupon, the ingredient having stimulative effect needs be found which will obtain a universal stimulative effect. Then, the effective amount of this ingredient was needed to be combined into perfume composition. From such a background, for example, the Japanese Unexamined Patent Publication No. Hei. 1-254629 reported that a fraction ingredient of lemon oil obtained by the distillation under reduced pressure has the effect that uplifts the conscious standard. Also, the patent publication reported that the awakening effect is obtained by evaporation followed by inhalation after addition of an effective amount of this fraction ingredient of lemon oil to a perfume. Also, in the Japanese Unexamination Patent Publication No. Hei. 6-172781, it is reported that completely pure 1,3-dimethoxy-5-methylbenzene solely shows the sedative effect. Further, a perfume composition including the effective amount of this compound is reported to have the sedative effect.

However, such a pure compound having an excellent stimulative effect is rarely known. Many aroma ingredients are required to find in consideration with the preference of the aroma. The stimulative agent and the stimulative perfume composition having excellent stimulative effect are required to develop by combinations of effective amounts.

SUMMARY OF THE INVENTION

The present invention is achieved in view of the foregoing prior art. An object of the present invention to provide a stimulative agent having an excellent stimulative effect. It is another object of the invention to provide a stimulative perfume composition having an excellent stimulative effect.

The present inventors have discovered that anisaldehyde which is one ingredient in essential oil of anise (*Pimpinella anisum*), has an excellent stimulative effect. Also, the present inventors have discovered that perfume compositions including an effective amount of anisaldehyde have the excellent stimulative effect. Furthermore, the inventors have discovered that the perfume composition including specific perfume added to this anisaldehyde has a more excellent stimulative effect.

Namely, a stimulative agent of the present invention comprises an anisaldehyde.

Also, a stimulative perfume composition of the present invention includes the anisaldehyde as an effective ingredient.

It is also preferable that the stimulative perfume composition of the present invention includes 0.01 wt % to 50 wt % of anisaldehyde in a stimulative perfume composition.

It is also preferable that the stimulative perfume composition of the present invention includes 1 wt % to 50 wt % of anisaldehyde in perfume ingredients of the stimulative perfume composition.

Also, in the present invention, it is also preferable that the stimulative perfume composition includes a perfume compound selected from the group consisting of cinnamic aldehyde, anethole, eugenol, carvone and heliotropin.

Also, in the stimulative perfume composition of the present invention, it is also preferable that a weight ratio of anisaldehyde to anethole is 1:10 to 1:1.

Also, in the stimulative perfume composition of the present invention, it is also preferable that a weight ratio of anisaldehyde to eugenol is 1:10 to 1:1.

Also, in the stimulative perfume composition of the present invention, it is also preferable that a weight ratio of anisaldehyde to cinnamic aldehyde is 1:10 to 1:1.

Also, in the present invention, it is also preferable that further the stimulative perfume composition includes a perfume composition selected from the group consisting of cinamon, star anise, clove and caraway.

Also, in the present invention, it is also preferable that further the stimulative perfume composition includes a perfume composition selected from the group consisting of pepper, cardamon and nutmeg.

BEST MODE OF THE INVENTION

Figure 1:
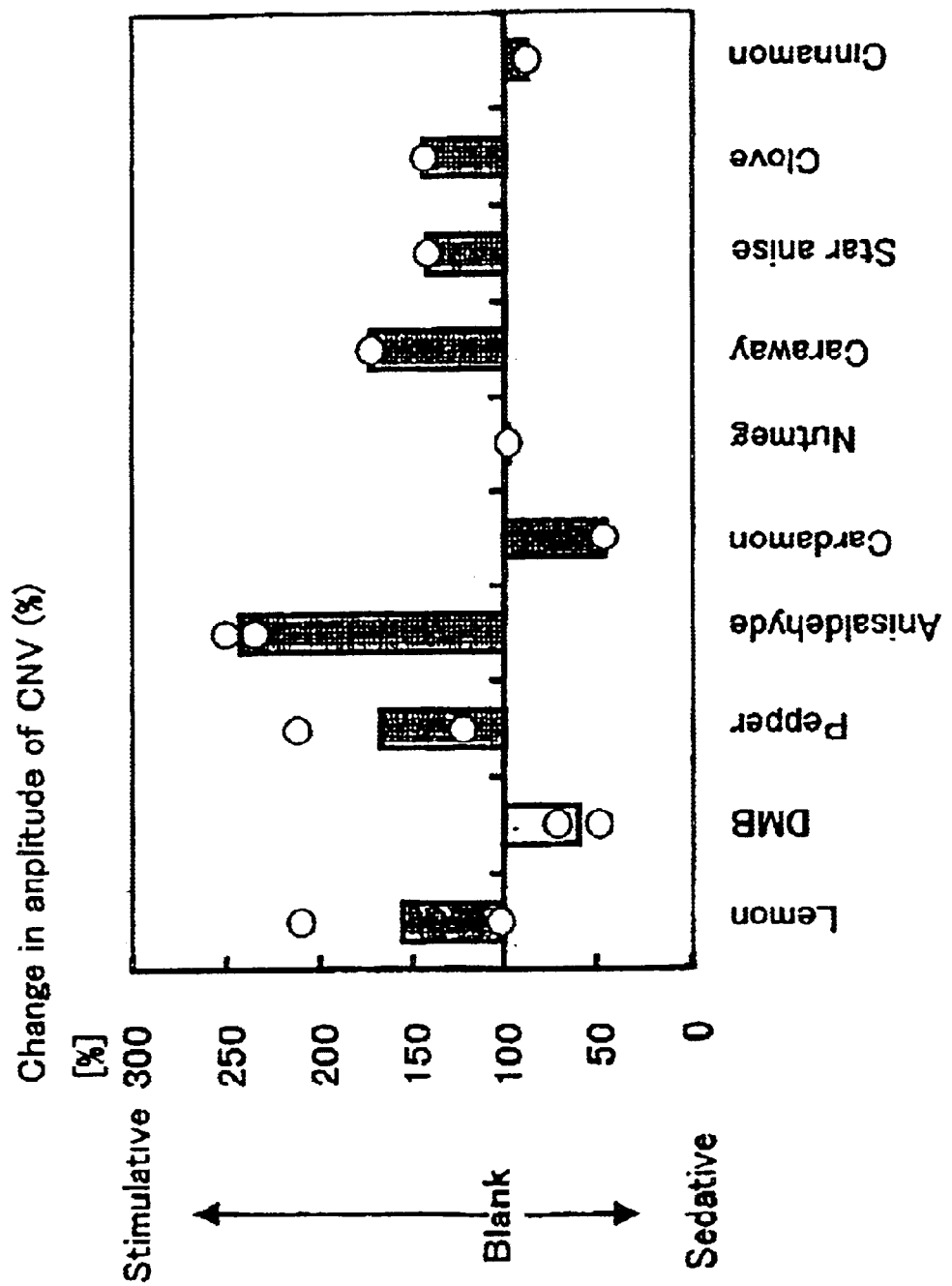
FIG. 1 shows the measurement result of CNV with regard to anisaldehyde and other perfumes in the present invention.

The following is a detailed explanation of the invention.

A stimulative effect in the present invention means that persons or animals are released from a physiological mental condition of sleepiness, sense of fatigue and inactivity in daily life. Also, the stimulative effect in the present invention includes a mental activation and a mental refreshing effect.

Also, the stimulative effect of the stimulative agent and the stimulative perfume composition of the present invention are produced by the inhalation of an effective ingredient and by the stimulation of olfactory receptor or by the absorption to the inside of the body through the respiratory tract. Namely, the stimulative agent and the stimulative perfume composition of the present invention are used by inhalation after evaporation.

Also, a term, "perfume ingredients" used in the present invention indicates the perfume ingredients in which a solvent and a carrier etc. are eliminated. Accordingly, the perfume ingredients are the component which includes only the aroma ingredient. However, essential oils include as perfume ingredients.

Anisaldehyde of the present invention, in other words, p-methoxy benzaldehyde used in the present invention is marketed as a perfume. This compound has a dry grass fragrance, and has strong sweet and slight cresol smell. Anisaldehyde produced by purification and isolation from natural essential oil can be also used. This natural essential oil for production of anisaldehyde is anise oil or star anise oil etc. Perfume ingredients of anise oil or star anise oil usually include about 0.5 wt % of anisaldehyde. The stimulative agent of the present invention comprises this anisaldehyde. The stimulative perfume composition of the present invention includes anisaldehyde as an effective ingredient. However, an amount of anisaldehyde in perfume ingredients of this natural essential oil has not excellent stimulative effect of the present invention (See Table 2).

Anisaldehyde of the present invention has strong aroma itself. Since pure anisaldehyde does not have a good fragrance, the use of the perfume composition including another perfume is desirable in order to provide a high-preference for the aroma (See Table 3). The amount of anisaldehyde in the perfume ingredients in the stimulative perfume composition can be decided properly in according to the purpose of use. Usually the preferable amount is 1 wt % to 50 wt % of anisaldehyde and 1 wt % to 20 wt % of anisaldehyde is more preferable. The stimulative perfume composition of the present invention is able to have an effective stimulative effect in 1 wt % or more of anisaldehyde in perfume ingredients. Although stimulative perfume compositions including over 50 wt % of anisaldehyde are possible, remarkable improvement of the stimulative effect may not be possible. It is unfavorable to add over 50 wt % of anisaldehyde, when the preference for aroma and the balance with other perfumes are considered. 1 wt % to 20 wt % of anisaldehyde are most preferable from the viewpoint of preference for the aroma. This amount of anisaldehyde can also demonstrate a sufficient stimulative effect.

Also, the amount of anisaldehyde in stimulative composition is preferably 0.01 wt % to 50 wt %. In the case where there is less 0.01 wt %, a sufficient stimulative effect may not be obtained. Although a perfume composition including over 50 wt % of anisaldehyde is possible, remarkable improvement of the stimulative effect may not be possible. It is unfavorable to add over 50 wt % of anisaldehyde when preference of aroma is considered.

The stimulative perfume composition of the present invention can include anisaldehyde and a specific perfume compound selected from the group consisting of cinnamic aldehyde, anethole, eugenol, carvone and heliotropin of the effective ingredient. The stimulative perfume composition including one or more of these specific perfume compounds can obtain a synergistic improvement in the stimulative effect (Stimulative synergistic effect). These perfume compounds are marketed as synthetic perfume.

In the case where the stimulative perfume composition includes one or more of these perfume compounds, although the amount of the specific perfume compound depends on kind of perfume compound, approximately 1 wt % to approximately 20 wt % of perfume compound in the perfume ingredients is preferable. In the case of less than 1 wt % of the specific perfume compound, the stimulative synergistic effect may be unobtainable. Over 20 wt % of the specific perfume compound does not show a tendency of large improvement of the stimulative effect.

Also, when one or more of anethole, eugenol and- cinnamic aldehyde are selected, a suitable weight ratio of the specific perfume compound exists for stimulative synergistic effect. In the case where anethole is selected, the weight ratio of anisaldehyde to anethole is preferably 1:10 to 1:1. Also, in the case where eugenol is selected, the weight ratio of anisaldehyde to eugenol is preferably 1:10 to 1:1. Also, in the case where cinnamic aldehyde is selected, the weight ratio of anisaldehyde to cinnamic aldehyde is preferably 1:10 to 1:1. In the case where the range is outside these weight ratios, the stimulative synergistic effect may be unobtainable, although the stimulative effect is obtained.

Also, the stimulative perfume composition of the present invention can have a stimulative synergistic effect by including the effective ingredient anisaldehyde and the specific perfume composition selected from the group consisting of cinnamon, star anise, clove, caraway, pepper, cardamon and nutmeg, which are usually marketed.

As each specific perfume composition that can give a stimulative synergistic effect, usual essential oil can be used. This essential oil is not restricted as far as the specific perfume composition is used. The followings are brief explanation of these specific perfume compositions.

Cinnamon is also called "Seiron Nikkei". For example, cinnamon in the present invention can use the essential oil that is obtained by steam distillation from bark or leaf of *Cinnamomum zeylanicum* which belongs to *Cinnamomum*.

Staranis is called Chinese anise or "Daiuikyou" or "Toushikimi". For example, star anise in the present invention can use the essential oil obtained by steam distillation from the fruit of *Illicium verum* which belongs to *Illicium*.

Clove is also called "Chouzi" or "Choukou". For example, clove in the present invention can use the essential oil that is obtained by steam distillation from the bud immediately before the bloom of *Syzygium aromaticum* (L.) (*Eugenia caryophyllata* Thunb.) which belongs to *Syzygium*.

Caraway is also called "Himeuikyou". For example, caraway in the present invention can use the essential oil that is obtained by steam distillation from the fruit of *Carum carvi* which belongs to umbelliferae.

Pepper is also called "Kosyou". For example, pepper in the present invention can use the essential oil that is obtained by steam distillation from the fruit of *Piper nigrum* L. which belongs *Piper*. White pepper or black pepper can be use in the present invention.

Cardamon is also called cardamom or cardarnum. This seed is called "Syouzuku" or "Byakuzuku". For example, cardamon in the present invention can use the essential oil that is obtained by steam distillation from the fruit of *Elettaria cardamomum* Maton which belongs to *Elettaria*.

Nutmeg is also called mace or "Nikuzuku". For example, nutmeg in the present invention can use the essential oil that is obtained by steam distillation from the fruit of *Myristica fragrans* which belongs to Myristicaceae.

In said perfume composition, cinnamon, star anise, clove and caraway contain cinnamic aldehyde, anethole, eugenol and carvone respectively, as the principal ingredient Also, the other perfume compositions where the synergistic effect is obtained are jasmin, carnation, estragon, basil, cascarilla, pimentoberry, ginger, calamus and cumin.

The preferable amount of the specific perfume composition giving the synergistic effect in the perfume ingredients is approximately 1 wt % to approximately 20 wt %, although it differs with the kind of perfume composition.

In addition to anisaldehyde of the said effective ingredient and the perfume giving the synergistic effect, as occasion requires, the stimulative perfume composition of the present invention can include a back-up component. The stimulative perfume composition of the present invention is used in perfume, cologne, shampoo, rinse and so on, skin care article, body shampoo, body rinse, body powder and so on, aromatic, deodorant and bath additives etc.

The following are the descriptions of the preferred embodiments of the stimulative agent and stimulative perfume composition of the present invention. The present invention is not restricted to these described below.

First of all, the test method of this invention is explained. The change of negative electric potential of brain called Contingent Negative Variation (CNV) was measured. CNV is the gradual fluctuation of electric potential of the brain. It is related to the fluctuation of the mental process and the conscious level such as an attention, expectation and anticipation.

An experiment to study perfume effects was as follows. After two seconds from a warning sound stimulation, a starting signal light of an exercise is turned on. Then, as soon as light is observed, the pushing button behavior is demanded as exercise reaction. In this series of steps, a sample, of aroma is located at 10 cm before nose tip. The aroma can be always recognized along with breathing. A recording electrode for the CNV measurement is fixed to the frontal region of the head. An electric potential between the frontal region and ear lobe is measured. In the case where caffeine having a stimulative effect was administered, the increase of amplitude of CNV was reported. In the case where nitrazepam having a sedative effect was administered, the decrease of amplitude of CNV was reported.

These fluctuations appear obviously in the early component of 400 to 1000 msec, after sound stimulation (not shown). The fluctuation area of this section is expressed as comparative percentage (%) to 100% of blank (odorless stimulation). Also, aroma was presented in accordance with Latin square method.

Figure 2:
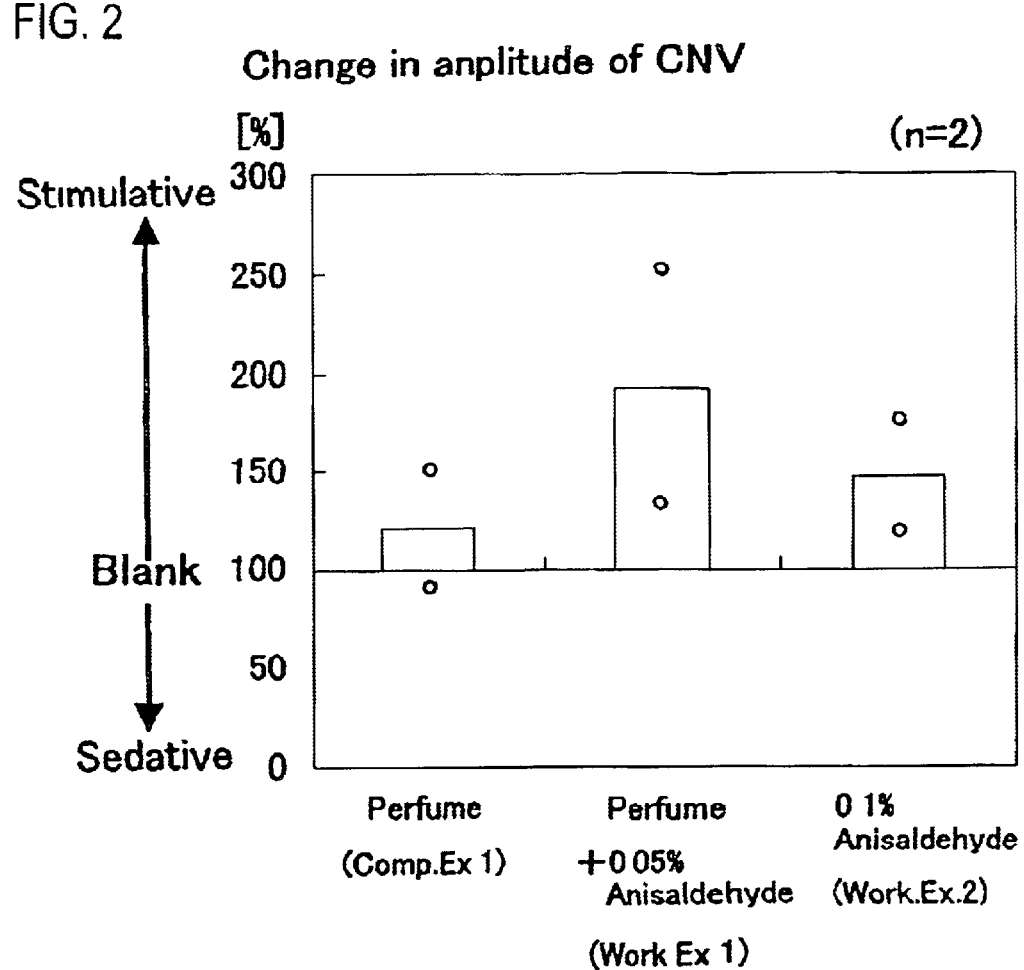
FIG. 2 shows the measurement result of CNV with regard to anisaldehyde and other perfume compositions in the present invention.

Over 100% of CNV (%) is shown to have the stimulative effect (See FIGS. 1 and 2). In the case of less than 100% of CNV (%), it shows that there is sedative effect. As a result of the detailed survey using CNV measurement for many natural essential oils, it is revealed the existence of essential oils possessing sedative effect or stimulative effect.

Confirmation of Stimulative Effect in the Present Invention

Samples were anisaldehyde of the present invention, 1,3-dimethoxy-5-methylbenzene (DMB) having sedative effect, lemon oil, pepper oil, cardamon oil, nutmeg oil, caraway oil, star anise oil, clove oil and cinnamon oil of natural essential oil. The CNV was measured using a 1% ethanol solution of each sample. The test was carried out by the above-mentioned method for 5 healthy adult women subjects. The result is shown in FIG. 1 in which the stimulative effect of lemon oil was confirmed in accordance with the tradition. The sedative effect of DMB was confirmed as described in the Japanese Unexamined Patent Publication No. Hei.6-172781. Also, the stimulative effect of pepper oil, caraway oil, star anise oil and clove oil was confirmed. Nutmeg oil was found to have neither stimulative effect nor sedative effect, while cinnamon oil was found to have a little sedative effect. Cardamon oil was confirmed to have clearly a sedative effect. Also, anisaldehyde of the present invention was confirmed to have a much stronger stimulative effect in comparison with conventional lemon oil (See FIG. 1).

Next, the change of the stimulative effect in case of compositions including anisaldehyde of the present invention and perfume composition was measured by observing the influence on CNV. Samples were perfume composition without anisaldehyde, perfume composition including 0.05 wt % of anisaldehyde and 0.1 wt % of anisaldehyde only (See FIG. 2). Each sample was measured was an ethanol solution. Furthermore, the combination amount (wt %) was calculated including solvent amount. Table 1 shows the detailed composition of the samples.

TABLE 1

|  | Comp. Ex. 1 | Work. Ex. 1 | Work. Ex. 2 |
| --- | --- | --- | --- |
| Cassis base | 0.015 | 0.015 | — |
| cis-3-Hexenol | 0.02 | 0.02 | — |
| Citronellol | 0.15 | 0.15 | — |
| Ethyl linalool | 0.25 | 0.25 | — |
| Ylang ylang oil | 0.015 | 0.015 | — |
| Methyl dihydrojasmonate | 1 | 1 | — |
| α-Hexylcinnamic aldehyde | 0.15 | 0.15 | — |
| Methyl ionone | 0.15 | 0.15 | — |
| 3-Cyclohexene-1-carboxyaldehyde | 0.6 | 0.6 | — |
| Helional | 0.1 | 0.1 | — |
| Jasmine absolute | 0.015 | 0.015 | — |
| Rose oil | 0.01 | 0.01 | — |
| Rose base | 0.1 | 0.1 | — |
| Muguet base | 0.225 | 0.225 | — |
| Hyacinth base | 0.15 | 0.15 | — |
| Strallyl acetate | 0.025 | 0.025 | — |
| Redberry oil | 0.025 | 0.025 | — |
| 7-Acetyl-1,2,3,4,5,6,7,8-octahydro-1,1,6,7-tetramethylnaphthalene | 0.15 | 0.15 | — |
| Cedryl methyl ketone | 0.2 | 0.2 | — |
| Star anise oil | 0.05 | 0.05 | — |
| 1,3,4,6,7,8-Hexahydro-4,6,6,7,8,8-hexamethyl-cyclopenta-gamma-2-benzopyrane | 1 | 1 | — |
| Ethylene brassylate | 0.5 | 0.5 | — |
| 3α,6,6,9α-Tetramethyl-dodecahydronaphthofuran | 0.05 | 0.05 | — |
| Anisaldehyde | 0 | 0.05 | 0.1 |
| Ethanol | 95.05 | 95.0 | 99.9 |
| Total | 100 | 100 | 100 |
| Amount (wt %) of anisaldehyde in perfume ingredients | 0 | 1 | 100 |

FIG. 2 shows the CNV measurement results. As revealed from FIG. 2, Working example 1 including perfume and anisaldehyde has a higher stimulative effect than Working example 2 including anisaldehyde only. Also, Working example 1 includes half the amount of anisaldehyde as compared with the case of Working example 2. Because there is not an outstanding stimulative effect in Comparative example 1 having perfume only, the synergistic effect is considered to be shown by combination of anisaldehyde and the perfume composition of Comparative example 1.

Therefore, it is shown that anisaldehyde of the present invention can reinforce the stimulative effect, when the compound is as a perfume composition.

Effective Amount of Anisaldehyde

Next, the inventors studied the effective amount of anisaldehyde of the present invention.

As samples, anethole, anethole including 0.5 wt % of anisaldehyde, anethole including 1 wt % of anisaldehyde and anethole including 5 wt % of anisaldehyde were used. Ethanol solution including 1 wt % of each sample was prepared and the influence on CNV shows measured. Table 2 shows the result.

TABLE 2

| Amount of anisaldehyde in perfume ingredients (wt %) | Measured value of CNV (%) |
|---|---|
| 0 | 108 |
| 0.5 | 118 |
| 1 | 136 |
| 5 | 138 |

From Table 2, it is shown that effective amount of anisaldehyde of the present invention in the perfume ingredients is 1 wt % or more. Because natural anise oil and star anise oil include 0.5 wt % of anisaldehyde in perfume ingredients at most, it is indicated that the excellent stimulative effect said in-the present invention is unobtainable with these natural oils.

Combination with Perfume

Next, the present inventors tested with regard to the stimulative synergistic effect of the stimulative perfume composition including anisaldehyde and natural perfume composition. Samples were (1) 1 wt % of perfume of combination object, (2) 0.1 wt % of anisaldehyde and (3) 0.5 wt % of object perfume and 0.05 wt % of anisaldehyde. All samples were used in an ethanol solution, and each measured CNV value (%) was obtained (CNV values are not shown). In the case where the value of (3) was larger than both those of (1) and (2), the stimulative synergistic effect was estimated to be "Yes" as indicated in Table 3. The amount (wt %) was calculated including the solvent amount.

Also, the estimation of the preference of aroma was carried out and the estimated criteria of aroma are as follows.

(Estimation Criteria of Preference for Aroma)

3 18 or more in 20 persons showed good preference for aroma.

2 11 to 17 in 20 persons showed good preference for aroma 1 6 to 10 in 20 persons showed good preference for aroma 0 5 or less in 20 persons showed good preference for aroma Table 3 shows the result.

TABLE 3

| Sample: Anisaldehyde + Perfume composition | Stimulative synergistic effect | Estimation of preference for aroma |
|---|---|---|
| Anisaldehyde + Cinnamon | Yes | 3 |
| Anisaldehyde + Star anise | Yes | 3 |
| Anisaldehyde + Clove | Yes | 2 |
| Anisaldehyde + Caraway | Yes | 2 |
| Anisaldehyde + Pepper | Yes | 2 |
| Anisaldehyde + Cardamon | Yes | 1 |
| Anisaldehyde + Nutmeg | Yes | 2 |

As shown in Table 3, the stimulative synergistic effect was confirmed with regard to sample including anisaldehyde and each perfume composition. Especially, strong stimulative synergistic effect was confirmed in pepper and clove. The stimulative synergistic effect was also observed both in nutmeg having no stimulative effect and in cardamon having sedative effect. Accordingly, it is shown that perfume composition combined with anisaldehyde does not relate to stimulation or sedation. However, anisaldehyde is required to be included in the effective amount in the perfume ingredients in order to obtain the stimulative synergistic effect.

Next, the inventors tested for the stimulative synergistic effect of the compositions including anisaldehyde and perfume compound. Samples were (1) 1 wt % of combination object perfume compound, (2) 0.1 wt % of anisaldehyde (Work.Ex.2) and (3) 0.5 wt % of combination object perfume compound and 0.05 wt % of anisaldehyde. CNV value (%) of the ethanol solution of each sample was measured (CNV values are not shown). In the case where the value of (3) was larger than those of both (1) and (2), the estimation of the stimulative synergistic effect was "Yes" as shown in Table 4. The amount (wt %) was calculated including the solvent amount.

Also, the estimation of the preference for aroma was carried out. The estimation criteria is as stated above. Table 4 shows the result.

TABLE 4

| Sample: Anisaldehyde + Perfume compound | Stimulative synergistic effect | Estimation of preference for aroma |
|---|---|---|
| Anisaldehyde + Cinnamic aldehyde | Yes | 3 |
| Anisaldehyde + Anethole | Yes | 3 |
| Anisaldehyde + Eugenol | Yes | 2 |
| Anisaldehyde + Carvone | Yes | 3 |
| Anisaldehyde + Heliotropin | Yes | 3 |

In Table 4, the stimulative synergistic effect was observed for all the perfume compositions including a specific perfume compound and anisaldehyde. The strongest stimulative synergistic effect was observed for eugenol and anisaldehyde.

Weight Ratio of Anisaldehyde to Specific Perfume Compound

Next, the present inventors combined various amounts of the specific perfume compound having the stimulative synergistic effect to anisaldehyde. Then, weight ratio influencing on the stimulative synergistic effect was studied. The concentration of anisaldehyde of the sample was fixed to 1 wt %. Changing the amount of the combination object perfume compound in the sample, CNV value in the weight ratio of each sample was measured. The estimation of the stimulative synergistic effect was carried out by comparing among the measured CNV value of 1 wt % of anisaldehyde in each sample (CNV values are not shown). In the case where CNV value of each sample is over CNV value of 1 wt % of anisaldehyde, the estimation of stimulative synergistic effect indicated as "Yes". The test was carried out for anethole, eugenol, cinnamic aldehyde in the perfume ingredient. The amount (wt %) was calculated including the solvent amount. Table 5 shows the results.

TABLE 5

| Sample:<br>Anisaldehyde +<br>Perfume compound | Weight ratio of amount<br>(Anisaldehyde:Perfume<br>compound) | Stimulative<br>synergistic<br>effect |
|---|---|---|
| Anisaldehyde + Anethole | 1:0.5 | No |
| | 1:1 | Yes |
| | 1:5 | Yes |
| | 1:10 | Yes |
| | 1:20 | No |
| Anisaldehyde + Eugenol | 1:0.5 | No |
| | 1:1 | Yes |
| | 1:5 | Yes |
| | 1:10 | Yes |
| | 1:20 | No |
| Anisaldehyde +<br>Cinnamic aldehyde | 1:0.5 | No |
| | 1:1 | Yes |
| | 1:5 | Yes |
| | 1:10 | Yes |
| | 1:20 | No |

In Table 5, in case of combining anisaldehyde with specific perfume compounds, preferable weight ratios of anisaldehyde to perfume compound were revealed as follows; anisaldehyde to anethole was approximately 1:1 to approximately 1:10, anisaldehyde to eugenol was approximately 1:1 to approximately 1:10, anisaldehyde to cinnamic aldehyde was approximately 1:1 to approximately 1:10.

The following description is the further embodiment of the present invention.

Working Example 3: Stimulative Perfume Composition

| | |
|---|---|
| Lemon oil | 5 (wt %) |
| Bergamot oil | 10 |
| Citronellol | 5 |
| Phenyl ethyl alcohol | 3 |
| Benzyl acetate | 3 |
| Methyl dihydrojasmonate | 20 |
| α-Hexyl cinnamic aldehyde | 5 |
| Hexyl salicylate | 5 |
| cis-3-Hexenyl salicylate | 4 |
| Lilial | 3 |
| Rose base | 4.5 |
| Muguet base | 4.0 |
| Jasmine absolute | 0.3 |
| Rose oil | 0.2 |
| Clove oil | 1.0 |
| Pepper oil | 1.0 |
| Anisaldehyde | 1 |
| Cedryl methyl ketone | 10 |
| Heliotropin | 1 |
| Coumarin | 3 |
| Ethylene brassylate | 10 |
| 3α,6,6,9α-Tetramethyldodecahydronaphthofuran | 1 |
| Total | 100 |

Working Example 4: Stimulative Perfume Composition

| | |
|---|---|
| Lemon oil | 12 (wt %) |
| Orange oil | 2 |
| Bergamot oil | 25 |
| Neroli oil | 2 |
| Petitgrain Bigarade | 1 |
| Methyl dihydrojasmonate | 20 |
| α-Hexyl cinnamic aldehyde | 6 |
| Geranium oil | 2 |
| Rosemary oil | 2 |
| Lavender oil | 3 |
| Dihydromycenol | 8 |
| Basil oil | 2 |
| Estragon oil | 1 |
| Anisaldehyde | 2 |
| Coumarin | 2 |
| Ethylene brassylate | 5 |
| 3α,6,6,9α-Tetramethyldodecahydronaphthofuran | 2 |
| Sandal wood oil | 2 |
| Oakmoss | 1 |
| Total | 100 |

Working Example 5: Stimulative Perfume Composition

| | |
|---|---|
| Cassis base | 0.3 (wt %) |
| Cis-3-Hexenol | 0.4 |
| Citronellol | 3 |
| Ethyl linalool | 5 |
| Ylang ylang oil | 0.3 |
| Methyl dihydrojasmonate | 20 |
| α-Hexyl cinnamic aldehyde | 3 |
| Methyl ionone | 3 |
| 3-cyclohexene-1-carboxyaldehyde | 12 |
| Helional | 2 |
| Jasmine absolute | 0.3 |
| Rose oil | 0.2 |
| Rose base | 2 |
| Muguet base | 4.5 |
| Hyacinth base | 3 |
| Strallyl acetate | 0.5 |
| Redberry oil | 0.5 |
| 7-Acetyl-1,2,3,4,5,6,7,8-octahydro-1,1,6,7-tetramethylnaphthalene | 3 |
| Cedryl methyl ketone | 4 |
| Anisaldehyde | 1.0 |
| Staranis oil | 1.0 |
| 1,3,4,6,7,8-Hexahydro-4,6,6,7,8,8-hexamethyl-cyclopenta-gamma-2-benzopyrane | 20 |
| Ethylene brassylate | 10 |
| 3α,6,6,9α-Tetramethyldodecahydronaphthofuran | 1 |
| Total | 100 |

Working Example 6: Bath Agent

| | |
|---|---|
| Sodium hydrogencarbonate | 70 (wt %) |
| Anhydrous sodium sulfate | 28.8 |
| Stimulative perfume composition (Work. Ex. 3) | 1 |
| Coloring pigment Y-202-1 | 0.2 |

After Components without perfume were agitated homogeneously by a V type mixer, the stimulative perfume composition was added. Then, this was agitated sufficiently until it became homogeneous. Thus, the bath agent was obtained.

Working Example 7: Gel type aromatic

| | |
|---|---|
| Carrageenan | 3.0 (wt %) |
| Propylene glycol | 2.0 |

| -continued | |
|---|---|
| Propylparaben | 0.3 |
| Stimulative perfume composition (Work. Ex. 3) | 5.0 |
| Water | 89.7 |

Carrageenan, propyleneglycol and propylparaben were mixed and water was added with agitation. This was heated to about 80° C. with calm agitation. Then, after this was cooled to about 65° C., a stimulative perfume composition was added with agitation of 3000 rpm by a homogenizer resulting a homogeneous phase. Then, this was poured to a specified container, and cooled at room temperature. Thus, a gel aromatic was obtained.

Working Example 8: Liquid Type Aromatic

| 95% Ethanol | 25.0 (wt %) |
|---|---|
| Surfactant | 5.0 |
| Stimulative perfume composition (Work. Ex. 3) | 3.0 |
| Water | 67.0 |

After each component without water was mixed, water was added with calm agitation resulting in a homogeneous phase. Thus, liquid aromatic was obtained. In this case, polyoxyethylene nonylphenylether EO-13 was used as a surfactant.

Working Example 9: Liquid Type Deodorant Agent

| Deodorant stock solution FS-500M (manufactured by Shiraimatsu shinyaku Co., LTD.) | 5.0 (wt %) |
|---|---|
| 95% Ethanol | 10.0 |
| Surfactant | 10.0 |
| 1% Anisaldehyde (Ethanol solution) | 10.0 |
| Water | 65.0 |

Each component without the water was mixed and water was added with calm agitation and the deodorant agent (Liquid type) was obtained. In this case, polyoxyethylene nonylphenylether EO-10 was used as a surfactant.

Working Example 10: Aerosol Type

| Deodorant stock solution FS-500M | 5.0 (wt %) |
|---|---|
| 95% Ethanol | 20.0 |
| 1% Anisaldehyde (Ethanol solution) | 10.0 |
| Water | 40.0 |
| Liquefied petroleum gas (4.0 kg/cm2 20° C.) | 25.0 |

Components without the liquefied petroleum gas were mixed and were agitated to make a homogeneous phase. After a specified quantity was inserted to an aerosol container and a valve was attached, liquefied petroleum gas was injected. Thus, the deodorant agent (aerosol type) was obtained.

As explained with the foregoing, a stimulative agent and a stimulative perfume composition including a stimulative agent of the present invention possess anisaldehyde as an effective ingredient. Accordingly, these have an aroma which is different from lemon which is known conventionally and they have an extremely high stimulative effect. Since a stimulative effect can be obtained by evaporation and inhalation only, the user has no need to be concerned about physical and psychological problems.

Also, a stimulative perfume composition of the present invention can include anisaldehyde and specific perfume compound or anisaldehyde and specific perfume composition. Thus a strong stimulative synergistic effect can be obtained.

What is claimed is:

1. A method of giving a stimulative effect to persons or animals by the evaporation and inhalation of a stimulative perfume composition that includes 0.01 wt % to 50 wt % of anisaldehyde.

2. The method according to claim 1, wherein the stimulative perfume composition includes 1 wt % to 50 wt % of anisaldehyde in perfume ingredients of the stimulative perfume composition.

3. The method according to claim 1, wherein the stimulative perfume composition further includes a perfume compound selected from the group consisting of cinnamic aldehyde, anethole, eugenol, carvone and heliotropin.

4. The method according to claim 3, wherein the stimulative perfume composition includes anisaldehyde and anethole, in a weight ratio of anisaldehyde to anethole is 1:10 to 1:1.

5. The method according to claim 3, wherein the stimulative perfume composition includes anisaldehyde and cinnamic aldehyde, in a weight ratio of anisaldehyde to cinnamic aldehyde is 1:10 to 1:1.

6. The method according to claim 1, wherein the stimulative perfume composition further includes a perfume composition selected from the group consisting of cinnamon, star anise, clove and caraway.

7. The method according to claim 1, wherein the stimulative perfume composition further includes a perfume composition selected from the group consisting of pepper, cardamon and nutmeg.

8. A method according to claim 1, wherein the persons or animals have a psychological mental condition of sleepiness, sense of fatigue, or inactivity in daily life.

9. A method of giving a stimulative effect to persons or animals by the evaporation and inhalation of stimulative perfume composition that includes anisaldehyde, and eugenol in a weight ratio of anisaldehyde to eugenol is 1:10 to 1:1.

* * * * *